United States Patent
Baudin et al.

(10) Patent No.: US 6,489,374 B1
(45) Date of Patent: Dec. 3, 2002

(54) PHOTOACTIVATABLE BASES CONTAINING NITROGEN

(75) Inventors: Gisèle Baudin, Allschwil (CH); Sean Colm Turner, Evanston, IL (US); Allan Francis Cunningham, Somers, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/763,108

(22) PCT Filed: Aug. 10, 1999

(86) PCT No.: PCT/EP99/05790

§ 371 (c)(1),
(2), (4) Date: Feb. 16, 2001

(87) PCT Pub. No.: WO00/10964

PCT Pub. Date: Mar. 2, 2000

(30) Foreign Application Priority Data

Aug. 21, 1998 (EP) .............................................. 98810819

(51) Int. Cl.$^7$ ........................... C08F 2/46; G03F 7/027; G03F 7/004; C09D 471/04; C09D 471/08; C08J 3/28; C07C 211/63

(52) U.S. Cl. ............................. 522/26; 522/28; 522/49; 522/50; 522/53; 522/56; 522/57; 522/62; 522/63; 522/65; 522/120; 522/121; 522/126; 522/129; 522/148; 522/167; 522/170; 522/174

(58) Field of Search ............................... 522/62, 63, 65, 522/49, 50, 56, 57, 26, 28, 53, 120, 121, 126, 129, 148, 167, 170, 174

(56) References Cited

U.S. PATENT DOCUMENTS

| | | | |
|---|---|---|---|
| 3,539,632 A | 11/1970 | Morris | 260/567.6 |
| 5,053,537 A | 10/1991 | Gitzel et al. | 564/8 |
| 5,475,119 A | 12/1995 | Baur et al. | 548/570 |
| 5,545,509 A | 8/1996 | Cameron et al. | 430/270.1 |
| 5,563,016 A * | 10/1996 | Baur et al. | 430/108.2 |
| 5,807,905 A | 9/1998 | Cunningham et al. | 522/25 |
| 6,057,380 A | 5/2000 | Birbaum et al. | 522/8 |
| 6,087,070 A | 7/2000 | Turner et al. | 430/280.1 |
| 2002/0076504 A1 * | 6/2002 | Klinkenberg et al. | 427/508 |

FOREIGN PATENT DOCUMENTS

| | | |
|---|---|---|
| EP | 0223587 | 5/1987 |
| EP | 0367164 | 5/1990 |
| EP | 0548826 | 6/1993 |
| EP | 0775706 | 5/1997 |
| GB | 2307474 | 5/1997 |
| WO | WO 98/41524 * | 9/1998 |

OTHER PUBLICATIONS

J. Gupton et al., J. Org.. Chem. (1987), vol. 52, pp. 3683–3686.
S. Mitra et al., JACS, vol. 101, (11), (1979), pp. 3097–3110.
D. R. McKean et al., Polym. Mat. Sci. vol. 66, (1992), pp. 237–338.
J. Cameron et al., J. Am. Chem. Soc., (1991), vol. 113, pp. 4303–4313.
J. Cameron et al., J. Am. Chem. Soc. (1996), vol. 118, pp. 12925–12937.
K.–I. Ito et al., Journal of Polymer Science, Part A, Polymer Chemistry, vol. 32, pp. 2177–2185, (1994).
T. Nishikubo et al., Polymer Journal, vol. 25, No. 4, pp. 421–425, (1993).
T. Nishikubo et al., Journal of Polymer Science, Part A: Polymer Chemistry Ed. 31 (1993), No. 12, pp. 3013–3020.
C. Kutal et al., J. Electrochem. Soc.: Solid–State Science and Technology, (1987), pp. 2280–2285.

* cited by examiner

Primary Examiner—Susan W. Berman
(74) Attorney, Agent, or Firm—Tyler A. Stevenson

(57) ABSTRACT

The invention relates to α-ammonium alkenes, iminium alkenes and amidinium alkenes in the form of their tetraaryl- or triaryl-alkylborate salts that can be converted photochemically into amines, imines or amidines, and to a process for the preparation thereof. The invention relates also to compositions polymerisable or crosslinkable under basic conditions comprising such α-ammonium alkenes, iminium alkenes or amidinium alkenes in the form of their tetra- or tri-arylalkylborate salts, to a method of carrying out photochemically induced, base-catalysed reactions, and to the use of such compounds as photoinitiators for base-catalysed reactions.

17 Claims, No Drawings

PHOTOACTIVATABLE BASES CONTAINING NITROGEN

The invention relates to α-ammonium alkenes, iminium alkenes and amidinium alkenes in the form of their tetraaryl- or triaryl-alkylborate salts, to a process for the preparation thereof, as well as to the photochemical cleavage thereof to form amines, imines or amidines and to the use thereof in systems crosslinkable by base catalysis or in hybrid systems (compositions crosslinkable or polymerisable both by free radicals and by base catalysis).

α-Ammonium alkene salts, especially 2-arylallylammonium salts, have already been described, for example in U.S. Pat. No. 3,539,632, J. Org. Chem. 52 (16) (1987), 3683 and in J. Am. Chem. Soc. 101 (11) (1979), 3097.

In addition to oligomers or monomers that are polymerisable by free radicals, systems catalysable by bases have also become known, especially for photolithographic procedures. Such systems require a photoinitiator which during irradiation splits off a base. R. MacKean et al., Polym. Mater. Sci. Eng. (1992), 66, 237–238, report, for example, on the photostructuring of polyimide, in which specific carbamates are used as photoinitiators.

The photolytic generation of bases and photopolymerisation reactions using those bases are also described, use being made of various types of photolabile compounds, e.g. carbamates (Cameron et al., U.S. Pat. No. 5,545,509 and references quoted therein; Cameron and Frechet, J. Am. Chem. Soc. (1991) 113, 4303), α-keto-carbamates (Cameron et al., J. Am. Chem. Soc. (1996) 118, 12925), O-acyloximes (Tsunooka et al., J. Polymer Sci.: Part A: Polymer Chem. (1994), 32, 2177), formamides (Nishikubo et al., Polym. J. (1993) 25, 421; idem, J. Polymer Sci.: Part A: Polymer Chem. (1993), 31, 3013) and co-amine complexes (C. Kutal et al. J. Electrochem. Soc. (1987), 134, 2280).

It has now surprisingly been found that certain α-ammonium alkenes, iminium alkenes and amidinium alkenes in the form of their tetraaryl- or triaryl-alkylborate salts split off an amine, imine or amidine group during irradiation with visible light or UV light. Those groups are sufficiently basic to trigger a plurality of base-catalysable reactions, especially polymerisation reactions. The compounds have a high level of sensitivity and their absorption spectrum can be varied within a wide range according to the substitution pattern chosen.

The compounds enable the preparation of so-called one-pot systems using base-catalysable oligomers or monomers, which have an extraordinarily high level of storage stability. For example polymerisation is not triggered until after irradiation. The systems can be formulated without or substantially without the use of solvents, since the compounds can be dissolved in the monomers or oligomers without any effect. The active catalyst is produced only after irradiation. Such systems can be used for a large number of purposes, for example for finishes, coatings, moulding materials or photolithographic images.

The invention relates to compounds of formula (I)

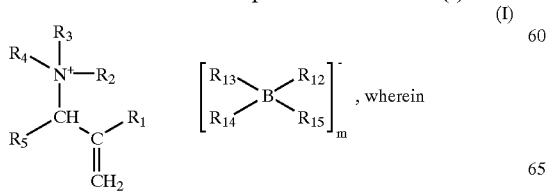

, wherein m is 1 or 2 and corresponds to the number of positive charges of the cation;

$R_1$ is phenyl, naphthyl, phenanthryl, anthracyl, pyrenyl, 5,6,7,8-tetrahydro-2-naphthyl, 5,6,7,8-tetrahydro-1-naphthyl thienyl, benzo[b]thienyl, naphtho[2,3-b]thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, those radicals being unsubstituted or mono- or poly-substituted by $C_1$–$C_{18}$alkyl, $C_3$–$C_{18}$alkenyl, $C_3$–$C_{18}$alkynyl, $C_1$–$C_{18}$haloalkyl, $NO_2$, $NR_6R_7$, $N_3$, OH, CN, $OR_8$, $SR_8$, $C(O)R_9$, $C(O)OR_{10}$ or by halogen, or $R_1$ is a radical of formula A or B

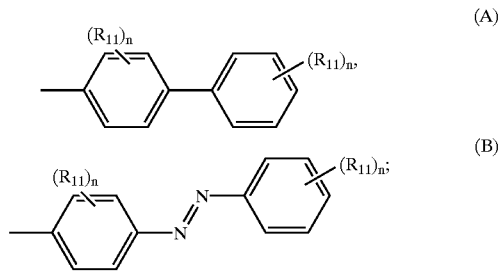

$R_2$, $R_3$ and $R_4$ are each independently of the others hydrogen, $C_1$–$C_{18}$alkyl, $C_3$–$C_{18}$alkenyl, $C_3$–$C_{18}$alkynyl or phenyl or, independently of one another, $R_2$ and $R_3$ and/or $R_4$ and $R_3$ form a $C_2$–$C_{12}$alkylene bridge; or $R_2$, $R_3$, $R_4$, together with the nitrogen atom to which they are bonded, form a phosphazene base of the type $P_1$, $P_2$, $P_4$ or a group of the structural formula (a), (b), (c), (d), (e), (f) or (g)

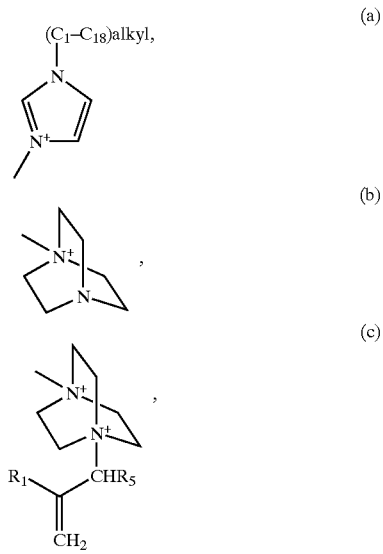

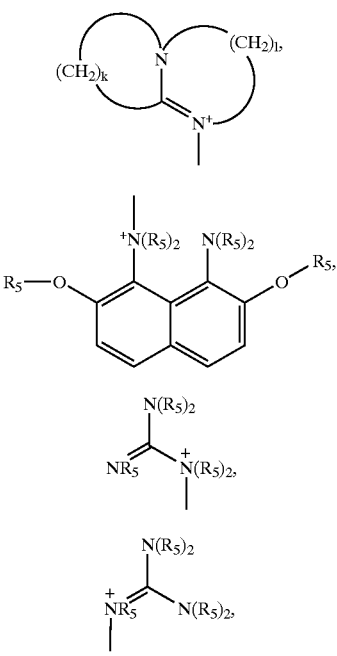

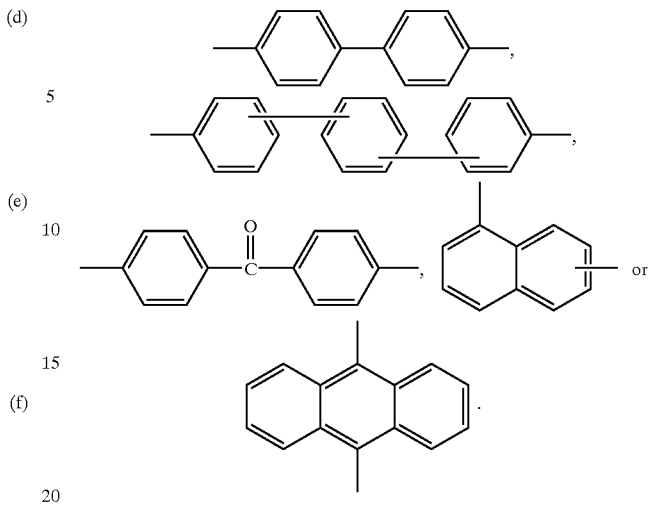

k and l are each independently of the other a number from 2 to 12;

$R_5$, $R_6$, $R_7$, $R_8$, $R_9$ and $R_{10}$ are each independently of the others hydrogen or $C_1$–$C_{18}$alkyl;

$R_{11}$ is $C_1$–$C_{18}$alkyl, $C_2$–$C_{18}$alkenyl, $C_2$–$C_{18}$alkynyl, $C_1$–$C_{18}$haloalkyl, $NO_2$, $NR_6R_7$, OH, CN, $OR_8$, $SR_8$, $C(O)R_9$, $C(O)OR_{10}$ or halogen, and n is 0 or a number 1, 2 or 3;

$R_{12}$, $R_{13}$ and $R_{14}$ are phenyl or another aromatic hydrocarbon, those radicals being unsubstituted or mono- or poly-substituted by $C_1$–$C_{18}$alkyl, $C_3$–$C_{18}$alkenyl, $C_3$–$C_{18}$alkynyl, $C_1$ $C_{18}$haloalkyl, $NO_2$, OH, CN, $OR_8$, $SR_8$, $C(O)R_9$, $C(O)OR_{10}$ or by halogen;

$R_{15}$ is $C_1$–$C_{18}$alkyl, phenyl or another aromatic hydrocarbon, the phenyl and aromatic hydrocarbon radicals being unsubstituted or mono- or poly-substituted by $C_1$–$C_{18}$alkyl, $C_3$–$C_{18}$alkenyl, $C_3$–$C_{18}$alkynyl, $C_1$–$C_{18}$haloalkyl, $NO_2$, OH, CN, $OR_8$, $SR_8$, $C(O)R_9$, $C(O)OR_{10}$ or by halogen, or $R_{15}$ is radical

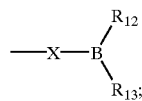

and

X is $C_1$–$C_{20}$alkylene, $C_2$–$C_{20}$alkylene interrupted by —O—, —S— or $NR_8$, or X is

By appropriate selection of the aromatic or heteroaromatic radical $R_1$ and of the borate anion, the absorption maximum can be varied within a wide range and thus the photosensitivity of the compounds can be shifted from UV into the daylight range.

Alkyl in the various radicals having up to 18 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl. Preference is given to alkyl having from 1 to 12 or from 1 to 8 carbon atoms, especially from 1 to 6 or from 1 to 4 carbon atoms.

Alkenyl having from 3 to 18 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. Preference is given to alkenyl having from 3 to 12 carbon atoms, especially from 3 to 6 carbon atoms. Alkynyl having from 3 to 18 carbon atoms is a branched or unbranched radical, for example propynyl (—$CH_2$—C≡CH ), 2-butynyl, 3-butynyl, n-2-octynyl or n-2-octadecynyl. Preference is given to alkynyl having from 3 to 12 carbon atoms, especially from 3 to 6 carbon atoms.

The $C_2$–$C_{12}$alkylene bridge is ethylene, propylene, butylene, pentylene, hexylene, heptylene, octylene, nonylene, decylene, undecylene or dodecylene.

Halogen is fluorine, chlorine, bromine or iodine.

Examples of $C_1$–$C_{18}$haloalkyl are wholly or partially halogenated $C_1$–$C_{18}$alkyl. Examples include the position isomers of mono- to deca-fluoropentyl, mono- to octa-fluorobutyl, mono- to hexa-fluoropropyl, mono- to tetra-fluoroethyl and mono- and di-fluoromethyl, as well as the corresponding chlorine, bromine and iodine compounds. Preference is given to the. perfluorinated alkyl radicals. Examples include perfluoropentyl, perfluorobutyl, perfluoropropyl, perfluoroethyl and especially trifluoromethyl.

Examples of the $NR_6R_7$ amino groups are the respective monoalkyl- or dialkyl-amino groups, such as methylamino, ethylamino, propylamino, butylamino, pentylamino, hexylamino, octadecylamino, dimethylamino, diethylamio, dipropylamino, diisopropylamino, di-n-butylamino, diisobutylamino, dipentylamino, dihexylamino or dioctadecylamino. Further dialkylamino groups include those in which the two radicals are each independently of the other branched or unbranched, for example methylethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, isopropyl-n-butylamino or isopropylisobutylamino.

The alkoxy group $OR_8$ having up to 18 carbon atoms is a branched or unbranched radical, for example methoxy, ethoxy, propoxy, isopropoxy, n-butoxy, isobutoxy, pentyloxy, isopentyloxy, hexyloxy, heptylbxy, octyloxy, decyloxy, tetradecyloxy, hexadecyloxy or octadecyloxy.

Preference is given to alkoxy having from 1 to 12 carbon atoms, especially from 1 to 8 carbon atoms, e.g. from 1 to 6 or from 1 to 4 carbon atoms.

Examples of the thioalkyl group $SR_8$ include thiomethyl, thioethyl, thiopropyl, thiobutyl, thiopentyl, thiohexyl, thioheptyl, thiooctyl and thiooctadecyl, in which the alkyl radicals may be linear or branched.

Aromatic hydrocarbons, as may be present, for example, in the compounds according to the invention ($R_{12}$, $R_{13}$, $R_{14}$ or $R_{15}$), may contain, for example, one or more, especially one or two, hetero atoms. There come into consideration as hetero atoms, for example, N, O, P and S, with preference being given to N and O. Examples of aromatic hydrocarbons include: phenyl, α- and β-naphthyl, stilbenyl, biphenyl, o-, m- and p-terphenyl, triphenylphenyl, binaphthyl, anthracyl, phenanthryl, pyrenyl, furan-2-yl and furan-3-yl, thiophen-2-yl and thiophen-3-yl, pyridin-2-yl, pyridin-3-yl and pyridin-4-yl, quinolyl and isoquinolyl.

Examples of the radical $R_1$ include phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphtho[2,3-b]-thienyl, thiathrenyl, dibenzofuryl, chromenyl, xanthenyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, stilbenyl, terphenyl, fluorenyl, phenoxazinyl, methoxyphenyl, 2,4-dimethoxyphenyl, 2,4,6-trimethoxyphenyl, bromophenyl, toluyl, xylyl, mesityl, nitrophenyl, dimethylaminophenyl, diethylaminophenyl, aminophenyl, diaminophenyl, 1-naphthyl, 2-naphthyl, 1-phenylamino-4-naphthyl, 1-methyinaphthyl, 2-methylnaphthyl, 1-methoxy-2-naphthyl, 2-methoxy-1-naphthyl, 1-dimethylamino-2-naphthyl, 1,2-dimethyl-4-naphthyl, 1,2-dimethyl-6-naphthyl, 1,2-dimethyl-7-naphthyl, 1,3-dimethyl-6-naphthyl, 1,4-dimethyl-6-naphthyl, 1,5-dimethyl-2-naphthyl, 1,6-dimethyl-2-naphthyl, 1-hydroxy-2-naphthyl, 2-hydroxy-1-naphthyl, 1,4-dihydroxy-2-naphthyl, 7-phenanthryl, 1-anthryl, 2-anthryl, 9-anthryl, 3-benzo[b]thienyl, 5-benzo[b]thienyl, 2-benzo[b]thienyl, 4-dibenzofuryl, 4,7-dibenzofuryl, 4-methyl-7-dibenzofuryl, 2-xanthenyl, 8-methyl-2-xanthenyl, 3-xanthenyl, 2-phenoxathiinyl, 2,7-phenoxathiinyl, 2-pyrrolyl, 3-pyrrolyl, 5-methyl-3-pyrrolyl, 2-imidazolyl, 4-imidazolyl, 5-imidazolyl, 2-methyl-4-imidazolyl, 2-ethyl-4-imidazolyl, 2-ethyl-5-imidazolyl, 3-pyrazolyl, 1-methyl-3-pyrazolyl, 1-propyl-4-pyrazolyl, 2-pyrazinyl, 5,6-dimethyl-2-pyrazinyl, 2-indolizinyl, 2-methyl-3-isoindolyl, 2-methyl-1-isoindolyl, 1-methyl-2-indolyl, 1-methyl-3-indolyl, 1,5-dimethyl-2-indolyl, 1-methyl-3-indazolyl, 2,7-dimethyl-8-purinyl, 2-methoxy-7-methyl-8-purinyl, 2-quinolizinyl, 3-isoquinolyl, 6-isoquinolyl, 7-isoquinolyl, isoquinolyl, 3-methoxy-6-isoquinolyl, 2-quinolyl, 6-quinolyl, 7-quinolyl, 2-methoxy-3-quinolyl, 2-methoxy-6-quinolyl, 6-phthalazinyl, 7-phthalazinyl, 1-methoxy-6-phthalazinyl, 1,4-dimethoxy-6-phthalazinyl, 1,8-naphthyridin-2-yl, 2-quinoxalinyl, 6-quinoxalinyl, 2,3-dimethyl-6-quinoxalinyl, 2,3-dimethoxy-6-quinoxalinyl, 2-quinazolinyl, 7-quinazolinyl, 2-dimethylamino-6-quinazolinyl, 3-cinnolinyl, 6-cinnolinyl, 7-cinnolinyl, 3-methoxy-7-cinnolinyl, 2-pteridinyl, 6-pteridinyl, 7-pteridinyl, 6,7-dimethoxy-2-pteridinyl, 2-carbazolyl, 3-carbazolyl, 9-methyl-2-carbazolyl, 9-methyl-3-carbazolyl, β-carbolin-3-yl, 1-methyl-β-carbolin-3-yl, 1-methyl-β-carbolin-6-yl, 3-phenanthridinyl, 2-acridinyl, 3-acridinyl, 2-perimidinyl, 1-methyl-5-perimidinyl, 5-phenanthrolinyl, 6-phenanthrolinyl, 1-phenazinyl, 2-phenazinyl, 3-isothiazolyl, 4-isothiazolyl, 5-isothiazolyl, 2-phenothiazinyl, 3-phenothiazinyl, 10-methyl-3-phenothiazinyl, 3-isoxazolyl, 4-isoxazolyl, 5-isoxazolyl, 4-methyl-3-furazanyl, 2-phenoxazinyl and 10-methyl-2-phenoxazinyl.

Examples of phosphazene bases of the $P_1$, $P_2$ or $P_4$ type include

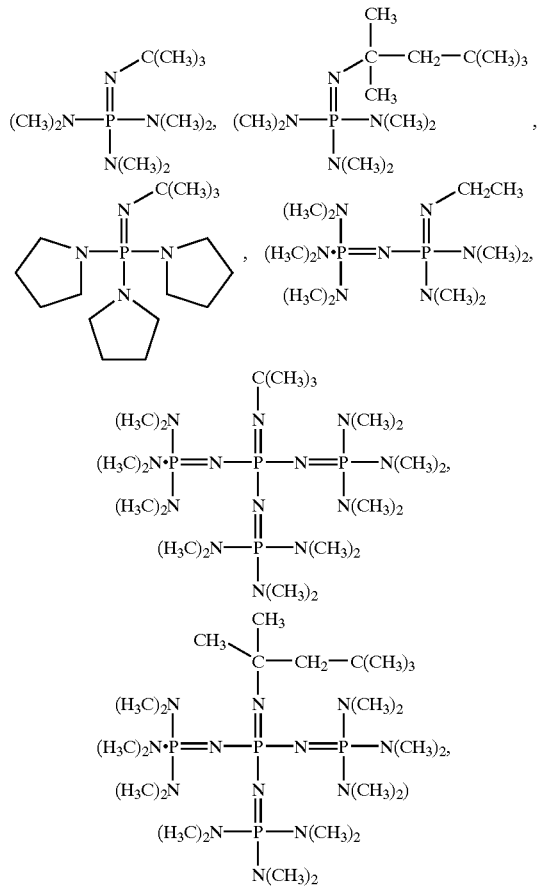

it being possible for the phosphazene bases to be bonded to the $CH_2$ group of the alkene either via the imine nitrogen or via one of the tertiary nitrogen atoms. They are preferably bonded to the $CH_2$ group of the ketone via one of the tertiary nitrogen atoms. Phosphazene bases of the $P_1$, $P_2$ or $P_4$ type are known to the person skilled in the art and are offered for sale, for example, in chemical catalogues. Examples of the nomenclature are in addition described in Angew. Chem. 1993, 105, 1420.

Preferably, $R_1$ is phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thiathrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, those radicals being unsubstituted or mono- or poly-substituted by $C_1$–$C_{18}$alkyl, $C_3$–$C_{18}$alkenyl, $C_3$–$C_{18}$alkynyl, $C_1$–$C_{18}$haloalkyl, $NO_2$, $NR_6R_7$, $N_3$, OH, CN, $OR_8$, $SR_8$, $C(O)R_9$, $C(O)OR_{10}$ or by halogen; or $R_1$ is a radical of formula A or B

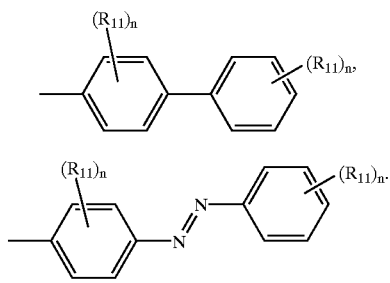

Especially preferably, $R_1$ is penyl, naphthyl, pyrenyl, thioxanthyl or phenothiazinyl, those radicals being unsubstituted or mono- or poly-substituted by $C_1$–$C_{18}$alkyl, $C_1$–$C_{18}$haloalkyl, $NR_6R_7$, CN, $NO_2$, $SR_8$ or by $OR_8$.

Especially preferably, $R_2$, $R_3$, and $R_4$ are each independently of the others hydrogen or $C_1$–$C_{18}$alkyl, or, independently, of one another, $R_2$ and $R_3$ and/or $R_4$ and $R_3$ form a $C_2$–$C_{12}$alkylene bridge; or $R_2$, $R_3$, $R_4$, together with the nitrogen atom to which they are bonded, form a group of the structural formula (a), (b), (c), (d), (e), (f) or (g), as indicated hereinbefore, or a phosphazene base of the type $P_1$, $P_2$ or $P_4$. k and 1 are each independently of the other a number from 2 to 12, preferably a number from 2 to 6.

Special preference is given to compounds wherein $R_2$, $R_3$ and $R_4$ are each independently of the others $C_1$–$C_{18}$alkyl or $R_2$, $R_3$, $R_4$, together with the nitrogen atom, form a group of the structural formula (a), (b), (c), (d) or (e), as indicated hereinbefore.

Preferably, $R_{12}$, $R_{13}$ and $R_{14}$ are phenyl, biphenyl, naphthyl, anthracyl or phenanthryl, those radicals being unsubstituted or mono- or poly-substituted by $C_1$–$C_{18}$alkyl, $C_1$–$C_{18}$haloalkyl, $NO_2$, OH, CN, $OR_8$ or by halogen, and $R_{15}$ is $C_1$–$C_{18}$alkyl, unsubstituted phenyl, or phenyl mono- or poly-substituted by $C_1$–$C_{18}$alkyl, $C_1$–$C_{18}$haloalkyl, $NO_2$, OH, CN, $OR_8$ or by halogen.

Suitable borate anions for the nitrogen base cation in the compounds of formula I are also disclosed, for example, in U.S. Pat. No. 4,772,530, GB 2 307 474, GB 2 307 473, GB 2 307 472 and EP 775 706. Examples include triphenylbutyl borate, triphenylhexyl borate, triphenylmethyl borate, dimesityl-phenyl-methyl or -butyl borate, di(bromomesityl)-phenyl-methyl- or -butyl borate, tris(3-fluorophenyl)hexyl borate, tris(3-fluorophenyl)-methyl or -butyl borate, dichloro-mesityl-phenyl-methyl or -butyl borate, tris (dichloromesityl)methyl borate, tris(3-chlorophenyl)hexyl borate, tris(3-chlorophenyl)-methyl or -butyl borate, tris(3-bromophenyl)hexyl borate, tris(3-bromophenyl)-methyl or -butyl borate, tris(3,5-difluorophenyl)hexyl borate, dimesityl-biphenyl-butyl borate, dimesityl-naphthyl-methyl or -butyl borate, di(o-tolyl)-9-anthracyl-methyl or -butyl borate, dimesityl-9-phenanthryl-phenyl or -butyl borate and

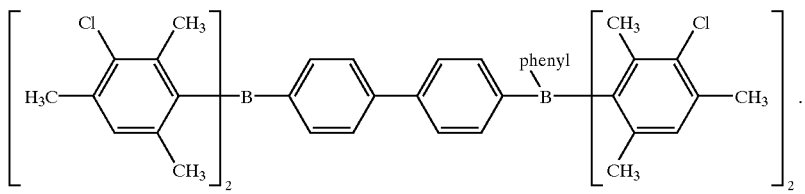

30

The preparation of such anions is decribed in the aforementioned publications.

The preparation of the bromides or iodides of the compounds of formula I according to the invention (=formula Ia and Ia', respectively), is carried out, for example, by reaction of an amine of formula II with an α-haloalkene of formula III

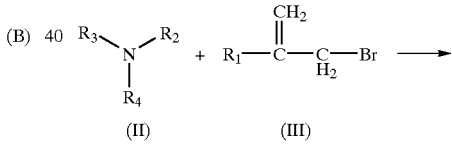

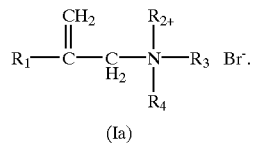

The halides can also be prepared, for example, by alkylation of an aromatically substituted α-aminoalkene:

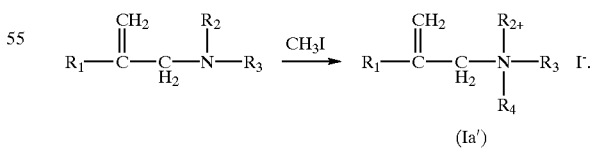

The borates can be obtained from the corresponding halides of the compounds according to the invention by anion exchange reaction. The reaction can be carried out in a manner known per se. Advantageously, a solvent or a mixture of solvents is co-used, for example water, hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

The reaction is advantageously carried out in a temperature range from −10° C. to +100° C. It is preferably carried out at from 10° C. to 50° C.

The invention relates also to a process for the preparation of compounds of formula I in which, in a first step, a nitrogen base of formula II $$NR_2R_3R_4 \tag{II}$$

is reacted with an α-haloalkene of formula III

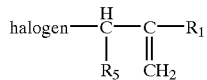
(III)

to form a compound of formula IV

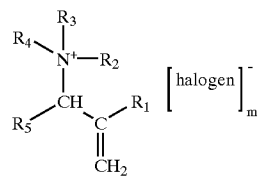
(IV)

and, in a second step, the compound of formula IV is reacted with a compound of formula V

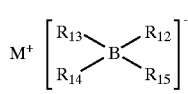
(V)

to form a compound of formula I wherein halogen is bromine or iodine and

M is sodium, potassium or ammonium, and the radicals $R_1$, $R_2$, $R_3$, $R_4$, $R_5$, $R_{12}$, $R_{13}$, $R_{14}$ and $R_{15}$ have the meanings, including the preferred meanings, given hereinbefore.

The invention relates also to a composition comprising

A) at least one compound of formula (I) as described hereinbefore and

B) at least one organic compound that is capable of a base-catalysed addition or substitution reaction.

Epoxy systems, for example, come into consideration as component B) in the compositions according to the invention. The epoxy resins customary in epoxy resin technology are suitable as component B) in the preparation of curable mixtures according to the invention with epoxy resins. Examples of such epoxy resins include:

I) Polyglycidyl and poly(β-methylglycidyl) esters, obtainable by the reaction of a compound having at least two carboxy groups in the molecule with epichlorohydrin or β-methylepichlorohydrin, respectively. The reaction is advantageously carried out in the presence of a base. An aliphatic carboxylic acid may be used as the compound having at least two carboxy groups in the molecule. Examples of such polycarboxylic acids include oxalic acid, succinic acid, glutaric acid, adipic acid, pimelic acid, suberic acid, azelaic acid and dimerised and trimerised linoleic acid. Cycloaliphatic polycarboxylic acids may also be used, for example tetrahydrophthalic acid, 4-methyltetrahydrophthalic acid, hexahydrophthalic acid or 4-methylhexahydrophthalic acid. In addition, aromatic polycarboxylic acids may be used, for example phthalic acid, isophthalic acid or terephthalic acid.

II) Polyglycidyl and poly(β-methylglycidyl) ethers, obtainable by the reaction of a compound having at least two free alcoholic hydroxy groups and/or phenolic hydroxy groups with epichlorohydrin or β-methylepichlorohydrin under alkaline conditions, or in the presence of an acid catalyst with subsequent alkali treatment. The glycidyl ethers of that type are derived, for example, from acyclic alcohols, such as ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol, sorbitol, and from polyepichlorohydrins, but may also be derived, for example, from cycloaliphatic alcohols, such as 1,4-cyclohexanedimethanol, bis(4-hydroxycyclohexyl)methane or 2,2-bis(4-hydroxycyclohexyl)propane, or they contain aromatic nuclei, such as N,N-bis(2-hydroxyethyl)aniline or p,p'-bis(2-hydroxyethylamino)diphenylmethane. The glycidyl ethers can also be derived from mononuclear phenols, for example from resorcinol or hydroquinone, or are based on polynuclear phenols, for example bis(4-hydroxyphenyl)methane, 4,4'-dihydroxybiphenyl, bis(4-hydroxyphenyl)sulfone, 1,1,2,2-tetrakis(4-hydroxyphenyl)ethane, 2,2-bis(4-hydroxyphenyl)propane, 2,2-bis(3,5-dibromo-4-hydroxyphenyl)propane or on novolaks, obtainable by the condensation of aldehydes, such as formaldehyde, acetaldehyde, chloral or furfuraldehyde, with phenols, such as phenol, or with phenols that are substituted in the nucleus by chlorine atoms or by $C_1$–$C_9$alkyl groups, for example 4-chlorophenol, 2-methylphenol or 4-tert-butylphenol, or by condensation with bisphenols, such as those of the above-mentioned kind.

III) Poly(N-glycidyl) compounds, obtainable by dehydrochlorination of the reaction products of epichlorohydrin with amines that contain at least two amine hydrogen atoms. Such amines include, for example, aniline, n-butylamine, bis(4-aminophenyl)methane, m-xylylenediamine and bis(4-methylaminophenyl)methane. The poly(N-glycidyl) compounds also include, however, triglycidyl isocyanurate, N,N'-diglycidyl derivatives of cycloalkylene ureas, such as ethylene urea or 1,3-propylene urea, and diglycidyl derivatives of hydantoins, such as 5,5-dimethylhydantoin.

IV) Poly(S-glycidyl) compounds, for example di-S-glycidyl derivatives derived from dithiols, e.g. ethane-1,2-dithiol or bis(4-mercaptomethylphenyl) ether.

V) Cycloaliphatic epoxy resins, for example bis(2,3-epoxycyclopentyl) ether, 2,3-epoxycyclopentylglycidyl ether, 1,2-bis(2,3-epoxycyclopentyloxy)ethane or 3,4-epoxycyclohexylmethyl-3',4'-epoxycyclohexanecarboxylate.

It is also possible, however, to use epoxy resins in which the 1,2-epoxy groups are bonded to different hetero atoms or functional groups; such compounds include, for example, the N,N,O-triglycidyl derivative of 4-aminophenol, the glycidyl ether-glycidyl ester of salicylic acid, N-glycidyl-N'-(2-glycidyloxypropyl)-5,5-dimethylhydantoin and 2-glycidyloxy-1,3-bis(5,5-dimethyl-1-glycidylhydantoin-3-yl)propane.

It is also possible to use mixtures of epoxy resins as component B). The invention accordingly relates also to a composition in which component B) is an epoxy resin or a mixture of different epoxy resins.

The base-catalysed addition or substitution reaction can be carried out with low molecular weight compounds (monomlers), with oligomers, with polymeric compounds or with a mixture of such compounds. Examples of reactions that can be carried out both with monomers and with oligomers/polymers using the photoinitiators according to the invention include the Knoevenagel reaction and Michael addition.

Of particular importance :are compositions in which component B) is an anionically polymerisable or crosslinkable organic material.

The organic material may be in the form of mono- or poly-functional monomers, oligomers or polymers.

Especially preferred oligomeric/polymeric systems are binders and surface-coating systems as conventionally used in the coating industry.

Examples of such base-catalysable binders and surface-coating systems are as follows:

a) acrylate copolymers having alkoxysilane or alkoxysiloxane side groups, for example the polymers described in U.S. Pat. No. 4,772,672 or 4,444,974;

b) two-component systems consisting of hydroxy-group-containing polyacrylates, polyesters and/or polyethers and aliphatic or aromatic polyisocyanates;

c) two-component systems consisting of functional polyacrylates and a polyepoxide, the polyacrylate containing carboxy or anhydride groups;

d) two-component systems consisting of fluorine-modified or silicone-modified hydroxy-group-containing polyacrylates, polyesters and/or polyethers and aliphatic or aromatic polyisocyanates;

e) two-component systems consisting of (poly)ketimines and aliphatic or aromatic polyisocyanates;

f) two-component systems consisting of (poly)ketimines and unsaturated acrylate resins or acetoacetate resins or methyl-α-acrylamido-methylglycolate;

h) two-component systems consisting of (poly) oxazolidines and anhydride-group-containing polyacrylates or unsaturated acrylate resins or polyisocyanates;

i) two-component systems consisting of epoxy-group-containing polyacrylates and carboxy-group-containing polyacrylates;

l) polymers based on allyl-glycidyl ether;

m) two-component systems consisting of a (poly)alcohol and a (poly)isocyanate; and n) two-component systems consisting of an α,β-ethylenically unsaturated carbonyl compound and a polymer containing activated $CH_2$ groups, the activated $CH_2$ groups being present either in the main chain or in the side chain or in both, as described, for example, in EP 161 697 for (poly)malonate groups. Other compounds having activated $CH_2$ groups are (poly)acetoacetates and (poly)cyanoacetates.

Among those base-catalysable binders, the following are especially preferred:

b) two-component systems consisting of hydroxy-group-containing polyacrylates, polyesters and/or polyethers and aliphatic or aromatic polyisocyanates;

c) two-component systems consisting of functional polyacrylates and a polyepoxide, the polyacrylate containing carboxy or anhydride groups;

i) two-component systems consisting of epoxy-group-containing polyacrylates and carboxy-group-containing polyacrylates;

m) two-component systems consisting of a (poly)alcohol and a (poly)isocyanate; and n) two-component systems consisting of an α,β-ethylenically unsaturated carbonyl compound and a polymer containing activated $CH_2$ groups, the activated $CH_2$ groups being present either in the main chain or in the side chain or in both. Other compounds having activated $CH_2$ groups are (poly)acetoacetates and (poly)cyanoacetates.

Two-component systems consisting of an α,β-ethylenically unsaturated carbonyl compound and a (poly)malonate and, the preparation thereof are described in EP 161 687. The malonate group can be bound in a polyurethane, polyester, polyacrylate, epoxy resin, polyamide or polyvinyl polymer either in the main chain or in a side chain. There may be used as α,β-ethylenically unsaturated carbonyl compound any double bond activated by a carbonyl group. Examples include esters and amides of acrylic acid or methacrylic acid. Additional hydroxy groups may also be present in the ester groups. Di- and tri-esters are also possible. Hexanediol diacrylate and trimethylolpropane triacrylate, for example, are typical. Instead of acrylic acid, other acids and their esters or amides may be used, such as, for example, crotonic acid or cinnamic acid.

The components of the system react with one another at room temperature under base catalysis, and form a crosslinked coating system that is suitable for numerous uses. On account of the fact that the system already has good fastness to weathering, it is also suitable, for example, for external use and can, if necessary, in addition be stabilised by UV absorbers and other light stabilisers.

The compositions comprise the photoinitiator, component A), preferably in an amount of from 0.01 to 10% by weight, based on component B).

The photopolymerisable mixtures may also contain various additives in addition to the photoinitiator, component A). Examples of such additives include thermal inhibitors, the purpose of which is to prevent premature polymerisation, for example hydroquinone, hydroquinone derivatives, p-methoxyphenol, β-naphthol and sterically hindered phenols, for example 2,6-di(tert-butyl)-p-cresol. In order to increase stability to dark storage, it is possible, for example, to use copper compounds, such as copper naphthenate, stearate or octanoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. In order to exclude atmospheric oxygen during polymerisation, paraffin or similar wax-like substances may be added which, being insufficiently soluble in the polymer, migrate to the surface at the beginning of the polymerisation and form a transparent surface layer which prevents the ingress of air. Equally possible is the application of a layer that is impermeable to oxygen. There may be added as light stabilisers, in a small amount, UV absorbers such as those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

The following are examples of such UV absorbers and light stabilisers:
1. 2-(2'-Hydroxyphenyl)-benzotriazoles, e.g. 2-(2'-hydroxy-5'-methylphenyl)-1, 2-(3',5'-di-tert-butyl-2'-hydroxyphenyl)-benzotriazole, 2-(5'-tert-butyl-2'-hydroxyphenyl)-benzo-triazole, 2-(2'-hydroxy-5'-(1,1,3,3-tetramethylbutyl)phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis(α,α-dimethylbenzyl)-2'-hydroxyphenyl)-benzotriazole, a mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)-carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2isooctyloxycarbonylethyl)phenyl-benzotriazole, 2,2'-methylene-bis[4-(1,1,3,3-tetramethylbutyl)-6-benzotriazol-2-yl-phenol]; the transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— wherein R=3'tert-butyl-4'-hydroxy-5'-2H-benzotriazol-2-yl-phenyl.
2. 2-Hydroxybenzophenone, e.g. the 4-hydroxy, 4-methoxy, 4-octyloxy, 4-decyloxy, 4-dodecyloxy, 4-benzyloxy, 4,2', 4'-trihydroxy or 2'-hydroxy-4,4'-dimethoxy derivative.
3. Esters of unsubstituted or substituted benzoic acids, e.g. 4-tert-butyl-phenyl salicylate, phenyl salicylate, octylphenyl salicylate, dibenzoylresorcinol, bis(4-tert-butylbenzoyl)-resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester and 3,5-di-tert-butyl-4-hydroxybenzoic acid 2-methyl-4,6-di-tertbutylphenyl ester.
4. Acrylates, e.g. α-cyano-β,β-diphenylacrylic acid ethyl ester or isooctyl ester, α-methoxycarbonylcinnamic acid methyl ester, α-cyano-βmethyl-p-methoxycinnamic acid methyl ester or butyl ester, α-methoxycarbonyl-p-methoxycinnamic acid methyl ester and N-(β-ethoxycarbonyl-β-cyanovinyl)-2-methyl-indoline.
5. Sterically hindered amines, e.g. bis(2,2,6,6-tetramethylpiperidyl)sebacate, bis(2,2,6,6-tetramethylpiperidyl)succinate, bis(1,2,2,6,6-pentamethylpiperidyl)sebacate, n-butyl-3,5-di-tert-butyl-4-hydroxybenzylmalonic acid bis(1,2,2,6,6-pentamethylpiperidyl) ester, the condensation product of 1-hydroxyethyl-2,2,6,6-tetramethyl-4-hydroxypiperidine and succinic acid, the condensation produkt of N,N'-bis (2,2,6,6-tetramethyl-4-piperidyl)hexamethylenediamine and 4-tert-octylamino-2,6-dichloro-1,3,5-s-triazine, tris (2,2,6,6-tetramethyl-4-piperidyl)nitrilotriacetate, tetrakis (2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-tri-azaspiro[4.5]decane-2,4-dione, bis (1-octyloxy-2,2,6,6-tetramethylpiperidyl)sebacate, bis(1-octyloxy-2,2,6,6-tetramethylpiperidyl)succinate, the condensation product of N,N'-bis(2,2,6,6-tetramethyl-4-piperidyl)hexamethylenediamine and 4-morpholino-2,6-dichloro-1,3,5-triazine, the condensation product of 2-chloro-4,6-di(4-n-butylamino-2,2,6,6-tetramethylpiperidyl)-1,3,5-triazine and 1,2-bis(3-aminopropylamino)ethane, the condensation product of 2-chloro-4,6di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)-pyrrolidine-2,5-dione and 3-dodecyl-1-(1,2,2,6,6-pentamethyl-4-piperidyl)-pyrrolidine-2,5-dione.
6. Oxalic acid diamides, e.g. 4,4'-dioctyloxy-oxanilide, 2,2'-diethoxy-oxanilide, 2,2'-dioctyloxy-5,5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl)oxalamide, 2-ethoxy-5-tert-butyl-2'-ethyl oxanilide and a mixture thereof with 2-ethoxy-2'-ethyl-5,4'-di-tert-butyl oxanilide and mixtures of o- and p-methoxy- and of o- and p-ethoxy-disubstituted oxanilides.
7. 2-(2-Hydroxyphenyl)-1,3,5-triazines, e.g. 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-di-hydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)-phenyl]-4,6-bis(2,4-dimethylphenyl)-1,3,5-triazine, 2-[2-hydroxy-4-(2-hydroxy-3-octyloxy-propyloxy)-phenyl]-4,6-bis(2,4-dimethylphenyl)-1,3,5-triazine and 2-[4-dodecyloxy/tridecyloxy-(2-hydroxypropyl)oxy-2-hydroxyphenyl]-4,6-bis(2,4-dimethylphenyl)-1,3,5-triazine.
8. Phosphites and phosphohites, e.g. triphenyl phosphite, diphenylalkyl phosphites, phenyldialkyl phosphites, tris (nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl) pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl)-4, 4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite and bis(2,4-di-tert-butyl-6-methylphenyl)ethyl phosphite.

The following are examples of further additives:
Fillers and thickeners, e.g. calcium carbonate, silicates, glass fibres, glass beads, asbestos, talc, kaolin, mica, barium sulfate, metal oxides and hydroxides, carbon black, graphite, wood flour and other natural products in powder or fibre form, synthetic fibres.

Other additives, e.g. plasticisers, lubricants, emulsifiers, pigments, rheology-improving additives, catalysts, flow improvers, fluorescent whitening agents, flame retardants, antistatics, blowing agents.

In addition to the aforementioned additives, additional co-initiators may be present. Such co-initiators are usually dyes, which, for example, improve the total quantum yield by means of energy transfer or electron transfer. Suitable dyes that can be used as co-initiators include, for example, triarylmethanes, e.g. malachite green, indolines, thiazines, e.g. methylene blue, xanthones, thioxanthones, oxazines, acridines and phenazines, e.g. safranine, and rhodamines of formula

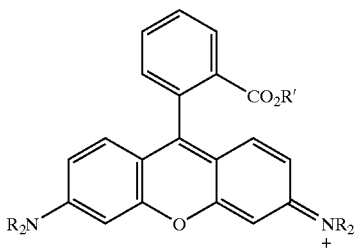

wherein R denotes alkyl or aryl radicals and R' is hydrogen, an alkyl radical or an aryl radical, e.g. rhodamine B, rhodamine 6G or violamine R, and furthermore sulforhodamine B or sulforhodamine G.

Preference is given to thioxanthones, oxazines, acridines, phenazines and rhodamines. Also suitable in that connection are combinations of dyes with borates, as described, for example, in U.S. Pat. No. 4,772,530, GB 2 307 474, GB 2 307 473, GB 2 307 472 and EP 775 706.

In addition to the afore-described base-catalysable (-curable) binders, component B), the composition may also comprise other binders. Possible other binders include, for example, other olefinically unsaturated compounds. The unsaturated compounds may contain one or more olefinic double bonds. They may be low molecular weight (monomeric) or higher molecular weight (oligomeric). Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate, and methyl and ethyl methacrylate. Also of interest are silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having several double bonds are ethylene glycol diacrylate, propylene glycol diacrylate, neopentyl glycol diacrylate, hexamethylene glycol diacrylate and bisphenol-A diacrylate, 4,4'-bis(2-acryloyloxyethoxy) diphenylpropane, trimethylolpropane triacrylate, pentaerythritol triacylate and pentaerythritol tetraacrylate, vinyl acrylate, divinyl benzene, divinyl succinate, diallyl phthalate, triallyl phosphate, triallyl isocyanurate and tris(2-acryloylethyl)isocyanurate.

Examples of higher molecular weight (oligomeric) poly-unsaturated compounds are acrylated epoxy resins, acrylated or vinyl-ether- or epoxy-group containing polyesters, polyurethanes and polyethers. Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl-ether and epoxide main chains. Combinations of vinylether-group-carrying oligomers and polymers, as described in WO 90/01512, are especially suitable, but copolymers of monomers functionalised with vinyl ether and maleic acid also come into consideration. Such unsaturated oligomers can also be termed prepolymers.

Especially suitable are, for example, esters of ethylenically unsaturated carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or m:ore such polymers.

When such free-radically curable monomers, oligomers/polymers are used in addition, it is advantageous, but not absolutely necessary, to add further photoinitiators that decompose yielding free radicals. Such photoinitiators are known and are produced industrially. Examples include benzophenone, benzophenone derivatives, acetophenone, acetophenone derivatives, e.g. α-hydroxycycloalkylphenyl ketones, dialkoxyacetophenones, α-hydroxy- and α-aminoacetophenones, 4-aroyl-1,3-dioxolanes, benzoin alkyl ethers and benzil ketals, monoacylphosphine oxides, bisacylphosphine oxides, ferrocenes and titanocenes.

Examples are mentioned in EP 284 561. Such polymer systems in which the curing/crosslinking is carried out according to different mechanisms are also termed hybrid systems.

Non-reactive binders may also be added to the compositions according to the invention, this being particularly advantageous when the photopolymerisable compounds are liquid or viscous substances. The amount of non-reactive binder may be, for example, from 5 to 95% by weight, preferably from 10 to 90% by weight and especially from 40 to 90% by weight, based on total solids. The choice of the non-reactive binder is made in accordance with the field of use and the properties required therefor, such as developability in aqueous and organic solvent systems, adhesion to substrates and sensitivity to oxygen.

Suitable binders are, for example, polymers having a molecular weight of approximately from 5000 to 2 000 000, preferably from 10 000 to 1 000 000. Examples are: homo- and copolymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, such as cellulose acetate, cellulose acetate butyrate, methylcellulose, ethylcellulose; polyvinylbutyral, polyvinylformal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylenelvinyl acetate), polymers such as polycaprolactam and poly(hexamethylene adipamide), polyesters such as poly(ethylene glycol terephthalate) and poly(hexamethylene glycol succinate).

The invention relates also to a method of carrying out base-catalysed reactions, which comprises irradiating a composition according to the invention as described hereinbefore with light of a wavelength of from 200 nm to 650 nm.

It may be advantageous in some cases for heating to be carried out during or after the irradiation. In that way the crosslinking reaction can be accelerated much more.

The photosensitivity of the compositions according to the invention usually extends from approximately 200 nm through the UV field into the infra-red range (approximately 20 000 nm, especially 1200 nm) and therefore covers a very broad range. Suitable radiation is present, for example, in sunlight or light from artificial light sources. Accordingly a large number of the most varied kinds of light source may be used. Both point sources and planiform radiators (lamp carpets) are suitable. Examples are: carbon arc lamps, xenon arc lamps, medium pressure, high pressure and low pressure mercury arc radiators, doped where appropriate with metal halides (metal halide lamps), microwave-excited metal vapour lamps, excimer lamps, superactinic fluorescent tubes, fluorescent lamps, argon incandescent lamps, electronic flash lamps, photographic floodlight lamps, electron beams and X-rays, produced by means of synchrotrons or laser plasma. The distance between the lamp and the substrate according to the invention to be irradiated may vary according to the intended use and the type and strength of the lamp and may be, for example, from 2 cm to 150 cm. Especially suitable are laser light sources, for example excimer lasers. Lasers in the visible range or the infra-red range may also be used. In that case the high level of sensitivity of the materials according to the invention and the possibility of matching a dyestuff, as co-initiator, to the laser line, are very advantageous. Printed circuits in the electronics industry, lithographic offset printing plates or relief printing plates and also photographic image-recording materials can be produced using this method.

The compositions according to the invention may be used for a variety of purposes, for example as printing inks, as clear lacquers, as white surface-coating compositions, for example for wood or metal, as paints inter alia for paper, wood, metal or plastics, as powder coating compositions, as daylight-curable paints for marking structures and roads, for photographic reproduction processes, for holographic recording materials, for image-recording processes or for the production of printing plates that can be developed using organic solvents or using aqueous-alkaline media, for the production of masks for screen printing, as dental filling compounds, as adhesives, as pressure-sensitive adhesives, as laminating resins, as etch or permanent resists and as solder masks for electronic circuits, in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibres and/or other fibres and other adjuvants) and other thick-layered compositions, in the coating or sealing of electronic components or as coatings for optical fibres.

In surface-coatings, use is frequently made of mixtures of a prepolymer with polyunsaturated monomers that also comprise a monounsaturated monomer, the prepolymer in particular determining the properties of the surface-coating film, so that a person skilled in the art will be able to influence the properties of the cured film by varying the prepolymer. The polyunsaturated monomer functions as a crosslinking agent, which renders the surface-coating film insoluble. The monounsaturated monomer functions as a reactive diluent, by means of which the viscosity is reduced without the need to use a solvent.

Unsaturated polyester resins are generally used in two-component systems together with a monounsaturated monomer, preferably styrene. For photoresists, specific one-component systems are often used, e.g. polymaleimides, polychalcones or polyimides, as described in DE 2 308 830. The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied by image-wise irradiation.

The substrates can be coated by applying a liquid composition, a solution or a suspension to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents include, for example, ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating methods, for example by spin-coating, immersion, knife coating, curtain pouring, brush application or spraying, especially by electrostatic spraying and reverse-roll coating, or by electrophoretic deposition. It is also possible to apply the photosensitive layer to a temporary flexible support and then coat the final substrate, e.g. a copper-clad circuit board, by transferring the layer by lamination.

The amount applied (layer thickness) and nature of the substrate (layer support) depend upon the desired field of use. The layer thickness range generally includes values of approximately from 0.1 $\mu$m to more than 100 $\mu$m.

The radiation-sensitive compositions according to the invention can also be irradiated image-wise, in which case they are used as negative resists. They are suitable for electronics (galvanoresists, etch resists, solder resists), for the production of printing plates, such as offset printing plates, flexographic and letterpress printing plates, or screen printing blocks, for the production of stamps, for use in the etching of mouldings or for use as microresists in the production of integrated circuits. The layer supports that are possible and the conditions for processing the coated substrates vary accordingly.

The expression "image-wise irradiation" includes irradiation using a photomask having a predetermined pattern, e.g. a diapositive, irradiation using a laser beam which is moved over the surface of the coated substrate, for example under computer control, and in that way produces an image, and irradiation with computer-controlled electron beams. After the image-wise irradiation of the material and prior to development, it may be advantageous to carry out a thermal treatment for a relatively short time. During the thermal treatment only the irradiated areas are thermally cured. The temperatures used are generally from 50 to 150° C., preferably from 80 to 130° C.; the duration of the thermal treatment is generally from 0.25 to 10 minutes.

Another field of use for photocuring is metal coating, for example in the application of a finish to metal sheets and tubes, cans or bottle closures, as well as photocuring on plastics coatings, for example of PVC-based floor or wall coverings. Examples of the photocuring of paper coatings include the application of a colourless finish to labels, record sleeves or book covers.

The invention relates also to the use of a compound of formula I as described hereinbefore as a photoinitiator for photochemically induced, base-catalysed addition or substitution reactions, especially for curing mouldings of composite materials, wherein the radicals $R_1$, $R_2$, $R_3$, $R_4$, $R_5$, $R_{12}$, $R_{13}$, $R_{14}$ and $R_{15}$ and m have the meanings and preferred meanings given hereinbefore.

The invention relates also to the above-mentioned use in the preparation of coatings, moulding materials or photostructured layers.

The composite material usually consists of a self-supporting matrix material, for example woven glass fibres, or alternatively, for example, plant fibres [see K.-P. Mieck, T. Reussmann in Kunststoffe 85 (1995), 366–370], which is impregnated with the photohardening formulation. Mouldings made of composite materials that have been produced using the compounds according to the invention have a high degree of mechanical stability and resistance. The compounds according to the invention can also be used as photohardeners in moulding, impregnating and coating materials, as described, for example, in EP 7086. Such materials are, for example, thin-layer resins, on which high demands are made in terms of curing activity and resistance to yellowing, and fibre-reinforced moulding materials, such as planar or longitudinally or transversely corrugated light panels.

Examples and preferred examples of base-catalysed addition and substitution reactions are mentioned hereinbefore. The invention relates also to a coated substrate that is coated on at least one surface with a composition as described above, and to a method for the photographic production of relief images, wherein a coated substrate is irradiated imagewise and then the non-irradiated portions are removed using a solvent. Of particular interest is the above-mentioned irradiation using a laser beam. The invention relates also to the use of the compounds according to the invention in the preparation of coatings, moulding materials or photostructured layers. The invention relates also to polymerised or crosslinked compositions according to the invention.

The following Examples further illustrate the invention. As in the remainder of the description and in the patent claims, unless otherwise indicated parts and percentages relate to weight. When alkyl or alkoxy radicals having more than three carbon atoms are mentioned without reference to their isomeric form, then the respective n-isomers are intended.

The following abbreviations are used in the Examples:
"Ar" denotes aryl, "DMSO" denotes dimethyl sulfoxide, "I.R." denotes infra-red spectra,
"$^1$H NMR" denotes hydrogen nuclear resonance spectra (displacement values quoted in ppm) and "m.p." denotes melting point.

EXAMPLES A

Preparation of Bromides

General procedure:

One equivalent of the nitrogen base in question is stirred in toluene at room temperature. One equivalent of 3-bromo-2-phenylpropene in toluene is added and the reaction mixture is stirred overnight. The precipitated bromide is filtered off and washed with toluene. The product is obtained in yields of from 60 to 70%.

Example A1

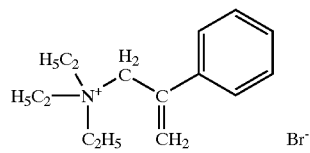

Analysis calculated for $C_{15}H_{24}BrN.1H_2O$: C, 56.97; H, 8.29; N, 4.43. Found: C, 56.92; H, 8.30; N, 4.19.

m.p.: 90–93° C.

I.R. (KBr) 1617 cm$^{-1}$.

$^1$H NMR (d$_6$-DMSO): 7.56 (2H, m, ArH), 7.40 (3H, m, ArH), 5.80 (1H, s, =CH), 5.74 (1H, s, =CH), 4.41 (2H, s, N$^+$—CH$_2$), 3.07 (6H, q, J=7.2 Hz), 1.11 (9H, t, J=7.1 Hz).

m/z (ESI-MS): 218 (ammonium cation); 79 and 81 (bromide anion).

Example A2

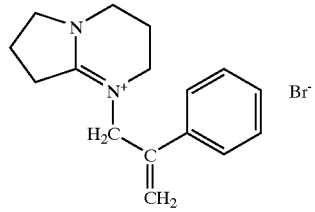

$^1$H NMR (d$_6$-DMSO): 7.52–7.10 (5H, m, ArH), 5.56 (1H, s, =CH), 5.24 (1H, s, =CH), 4.56 (2H, s, N$^+$—CH$_2$), 3.68 (2H, t, J=7.2 Hz), 3.38 (4H, m), 3.01 (2H, d, J=7.8 Hz), 2.05 (4H, m).

m/z: (ESI-TOF-MS): 241 (ammonium cation).

Examples B

Preparation of Borate Salts

General Procedure for the Preparation of Tetraphenylborate Salts

One equivalent of the bromide in question is stirred at room temperature in water and one equivalent of an aqueous solution of sodium tetraphenylborate is added. The precipitated tetraphenylborate salt is filtered off, washed with water and dried in vacuo. The product is obtained in a yield of 95%.

Example B1

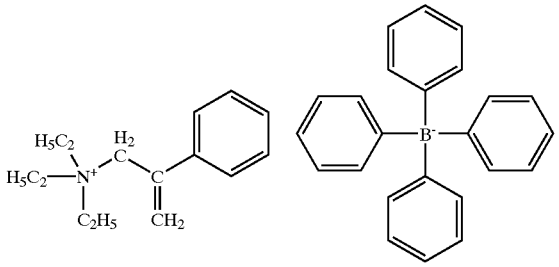

Analysis calculated for $C_{39}H_{44}BN.2H_2O$: C, 81.66; H, 8.43; N, 2.44. Found: C, 81.31; H, 7.94; N, 2.24.

m.p.=165–166° C. I.R. (KBr) 1579 cm$^{-1}$.

$^1$H NMR (d$_6$-DMSO): 7.55 (2H, m, ArH), 7.41 (3H, m, ArH), 7.17 (8H, m, ArH), 6.91 (12H, m, ArH), 5.79 (1H, s, =CH), 5.75 (1H, s, =CH), 4.38 (2H, s, N$^+$—CH$_2$), 3.07 (6H, q, J=7.2 Hz), 1.10 (9H, t, J=7.1 Hz).

m/z (ESI-TOF-MS): 218 (ammonium cation); 319 (borate anion).

Example B2

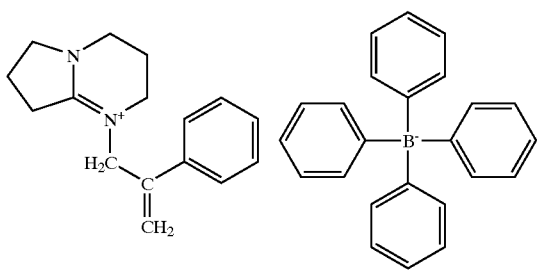

Analysis calculated for C$_{40}$H$_{41}$BN$_2$.0.4H$_2$O: C, 84.61; H, 7.42; N, 4.93. Found: C, 84.67; H 7.44; N, 4.76.

m.p.=141–142° C.

I.R. (KBr) 1673 cm$^{-1}$. $^1$H NMR (CDCl$_3$): 7.33 (11H, m, ArH), 7.10 (2H, m, ArH), 6.91 (12H, m, ArH), 5.37 (1H, s, =CH), 4.87 (1H, s, =CH), 3.61 (2H, s, N$^+$—CH$_2$), 2.92 (2H, t, J=7.2 Hz), 2.66 (2H, t, J=5.5 Hz), 2.48 (2H, t, J=5.8 Hz), 1.93 (2H, t, J=7.6 Hz), 1.51 (2H, m), 1.36 (2H, t, J=5.7 Hz).

m/z (ESI-MS): 241 (ammonium cation); 319 (borate anion).

Example B3

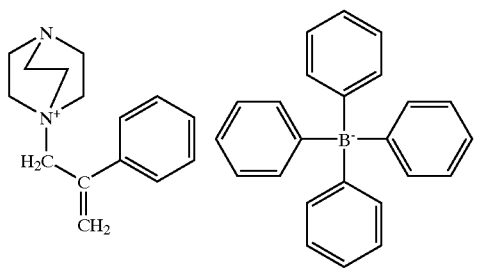

Analysis calculated for C$_{39}$H$_{41}$BN$_2$.0.75H$_2$O: C, 83.34; H, 7.62; N, 4.98; Found: C, 83.36; H, 7.49; N, 4.66.

m.p.=222–223° C.

$^1$H NMR (d$_6$-DMSO): 7.58 (2H, m, ArH), 7.42 (3H, m, ArH), 7.17 (8H, m, ArH), 6.92 (8H, m, ArH), 6.78 (4H, m, ArH), 5.93 (1H, s, =CH), 5.71 (1H, s, =CH), 4.43 (2H, s, N$^+$—CH$_2$), 3.14 (6H, m), 2.93 (6H, m).

m/z (ESI-TOF-MS): 229 (ammonium cation); 319 (borate anion).

General Procedure for the Preparation of the tris(3-fluorophenyl)hexylborate Salt One equivalent of the bromide in question is stirred at room temperature in water and one equivalent of a methanolic solution of tetramethylammonium tris(3-fluorophenyl)hexylborate is added. The precipitated tris(3-fluorophenyl)hexylborate salt is filtered off, washed with water and dried in vacuo. The product is obtained in a yield of 85%.

Example B4

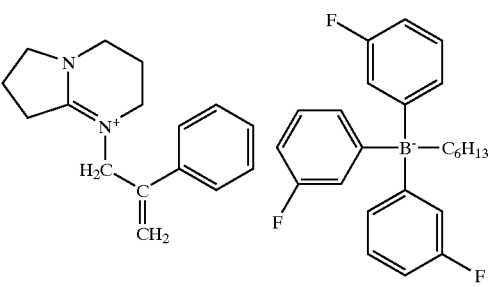

$^1$H NMR (d$_6$-DMSO): 7.43 (5H, m, ArH), 6.96 (9H, m, ArH), 6.53 (3H, m, ArH), 5.56 (1H, s, =CH), 5.21 (1H, s, =CH), 4.54 (2H, s, N$^+$—CH$_2$), 3.67 (2H, t, J=7.2 Hz), 3.34 (4H, m), 2.98 (2H, t, J=7.8 Hz), 1.97 (4H, m), 1.57 (6H, br. s.), 0.8 (7H, m).

m/z (ESI-TOF-MS): 241 (ammonium cation); 381 (borate anion).

Example B5

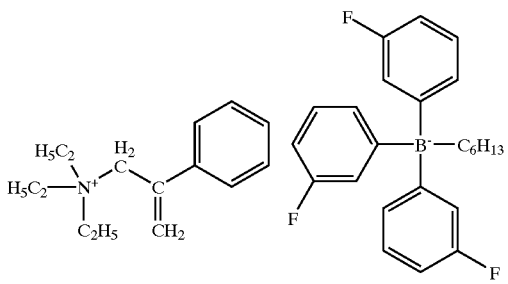

Analysis calculated for C$_{39}$H$_{49}$BF$_3$N: C, 78.12; H, 8.24; F, 9.50; N, 2.33. Found: C, 77.90; H, 8.32; F, 9.41; N, 2.80.

m.p.=72–74° C.

I.R. (KBr) 1594 cm$^{-1}$.

$^1$H NMR (d$_6$-DMSO): 7.55 (2H, m, ArH), 7.41 (3H, m, ArH), 6.95 (6H, m, ArH), 6.78 (3H, m, ArH), 6.55 (3H, m, ArH), 5.79 (1H, s, =CH), 5.75 (1H, s, =CH), 4.38 (2H, s, N$^+$—CH$_2$), 3.07 (6H, q, J=7.2 Hz), 1.12 (15H, m), 0.80 (7H, m).

m/z (ESI-TOF-MS): 218 (ammonium cation); 381 (borate anion).

Application Example C

Example C1

A composition is prepared by mixing the following components:

| | |
|---|---|
| 100.0 parts | epoxyphenol novolak ($^{RTM}$GY1180; Ciba Spezialitatenchemie) |
| 200.0 parts | polyacrylate containing carbonyl groups ($^{RTM}$CARBOSET 525; B.F. Goodrich) |
| 9.0 parts | latent base (=3%) |
| 1.5 parts | isopropylthioxanthone (ITX) (=0.5%) |
| 500.0 parts | acetone |

The formulation so obtained is applied to an aluminium sheet using a 100 μm spiral applicator and is dried at 50° C.

for 15 minutes. There is applied to that layer a polyester film and then a standardised test negative having 21 steps of different optical density (Stouffer wedge). The specimen is covered with a second UV-transparent film and pressed onto a metal plate by vacuum. The irradiation is carried out in a first series of tests for 80 seconds, and in a second series of tests for 160 seconds, and in a third series of tests for 320 seconds at a distance of 60 cm using a 3kW metal halide lamp (ORC SM×3000). After irradiation, the films and the mask are removed and the irradiated layer is developed in ethanol for 5 minutes in an ultrasound bath at 23° C. The drying is carried out at 120° C. for 5 minutes in a circulating air oven. The sensitivity of the initiator system used is characterised by the number of the last wedge step imaged tack-free. The higher the number of steps, the more sensitive the system tested. The results are shown in Table 1.

TABLE 1

| photoinitiator | number of imaged steps after | | |
|---|---|---|---|
| from Example | 80 sec. | 160 sec. | 320 sec. |
| B1 | 11 | 13 | 15 |
| B2 | 9 | 11 | 13 |

What is claimed is:
1. A compound of formula (I)

$$\begin{bmatrix} R_4 & R_3 \\ & | \\ & N^+ - R_2 \\ R_5 & | \\ & CH \\ & | & R_1 \\ & C \\ & || \\ & CH_2 \end{bmatrix} \begin{bmatrix} R_{13} & R_{12} \\ B \\ R_{14} & R_{15} \end{bmatrix}_m^-$$ (I), wherein m is 1 or 2 and corresponds to the number of positive charges of the cation;

R$_1$ is phenyl, naphthyl, phenanthryl, anthracyl, pyrenyl, 5,6,7,8-tetrahydro-2-naphthyl, 5,6,7,8-tetrahydro-1-naphthyl, thienyl, benzo[b]thienyl, naphtho[2,3-b]thienyl, thianthrenyl, dibenzofuryl, chromenyl, xanthenyl, thioxanthyl, phenoxathiinyl, pyrrolyl, imidazolyl, pyrazolyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, terphenyl, stilbenyl, fluorenyl or phenoxazinyl, those radicals being unsubstituted or mono- or poly-substituted by C$_1$–C$_{18}$alkyl, C$_3$–C$_{18}$alkenyl, C$_3$–C$_{18}$alkynyl, C$_1$–C$_{18}$haloalkyl, NO$_2$, NR$_6$R$_7$, N$_3$, OH, CN, OR$_8$, SR$_8$, C(O)R$_9$, C(O)OR$_{10}$ or by halogen, or R$_1$ is a radical of formula A or B (A)

(B)

R$_2$, R$_3$ and R$_4$ are each independently of the others hydrogen, C$_1$–C$_{18}$alkyl, C$_3$–C$_{18}$alkenyl, C$_3$–C$_{18}$alkynyl or phenyl or, independently of one another, R$_2$ and R$_3$ and/or R$_4$ and R$_3$ form a C$_2$–C$_{12}$alkylene bridge; or R$_2$, R$_3$, R$_4$, together with the nitrogen atom to which they are bonded, form a phosphazene base of the type P$_1$, P$_2$, P$_4$ or a group of the structural formula (a), (b), (c), (d), (e), (f) or (g)

(a)

(b)

(c)

(d)

(e)

(f)

(g)

k and l are each independently of the other a number from 2 to 12;

$R_5$, $R_6$, $R_7$, $R_8$, $R_9$ and $R_{10}$ are each independently of the others hydrogen or $C_1$–$C_{18}$alkyl;

$R_{11}$ is $C_1$–$C_{18}$alkyl, $C_2$–$C_{18}$alkenyl, $C_2$–$C_{18}$alkynyl, $C_1$–$C_{18}$haloalkyl, $NO_2$, $NR_6R_7$, OH, CN, $OR_8$, $SR_8$, $C(O)R_9$, $C(O)OR_{10}$ or halogen; and n is 0 or a number 1, 2 or 3;

$R_{12}$, $R_{13}$ and $R_{14}$ are phenyl or another aromatic hydrocarbon, those radicals being unsubstituted or mono- or poly-substituted by $C_1$–$C_{18}$alkyl, $C_3$–$C_{18}$alkenyl, $C_3$–$C_{18}$alkynyl, $C_1$–$C_{18}$haloalkyl, $NO_2$, OH, CN, $OR_8$, $SR_8$, $C(O)R_9$, $C(O)OR_{10}$ or by halogen;

$R_{15}$ is $C_1$–$C_{18}$alkyl, phenyl or another aromatic hydrocarbon, the phenyl and aromatic hydrocarbon radicals being unsubstituted or mono- or poly-substituted by $C_1$–$C_8$alkyl, $C_3$–$C_{18}$alkenyl, $C_3$–$C_{18}$alkynyl, $C_1$–$C_{18}$haloalkyl, $NO_2$, OH, CN, $OR_8$, $SR_8$, $C(O)R_9$, $C(O)OR_{10}$ or by halogen, or $R_{15}$ is a radical

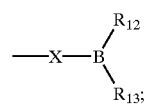

and

X is $C_1$–$C_{20}$alkylene, $C_2$–$C_{20}$alkylene interrupted by —O—, —S— or $NR_8$, or X is

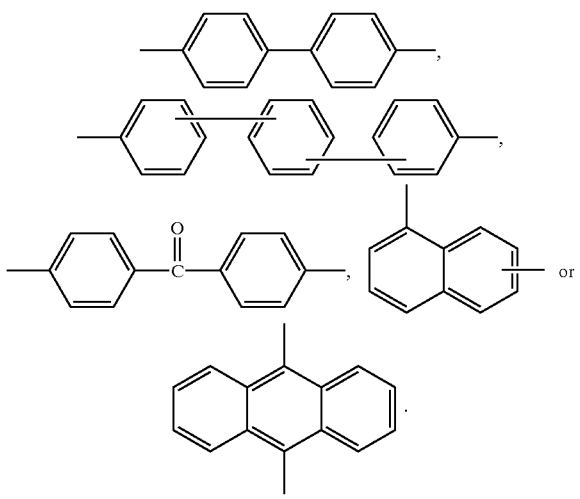

2. A compound according to claim 1, wherein $R_1$ is phenyl, naphthyl, pyrenyl, thioxanthyl or phenothiazinyl, those radicals being unsubstituted or mono- or poly-substituted by $C_1$–$C_{18}$alkyl, $C_1$–$C_{18}$haloalkyl, $NR_6R_7$, CN, $NO_2$, $SR_8$ or by $OR_8$.

3. A compound according to claim 1, wherein $R_2$, $R_3$ and $R_4$ are each independently of the others hydrogen or $C_1$–$C_{18}$alkyl, $R_2$ and $R_3$ and/or $R_4$ and $R_3$, independently of one another, form a $C_2$–$C_{12}$alkylene bridge, or $R_2$, $R_3$, $R_4$, together with the nitrogen atom to which they are bonded, form a group of the structural formula (a), (b), (c), (d), (e), (e, (g) or (h) or a phosphazene base of the type $P_1$, $P_2$ or $P_4$.

4. A compound according to claim 1, wherein $R_2$, $R_3$ and $R_4$ $C_1$–$C_{18}$alkyl, together with the nitrogen atom, form a group of the structural formula (a), (b), (c), (d) or (e).

5. A compound according to claim 1, wherein $R_{12}$, $R_{13}$ and $R_{14}$ are phenyl, biphenyl, naphthyl, anthracyl or phenanthryl, those radicals being unsubstituted or mono- or poly-substituted by $C_1$–$C_{18}$alkyl, $C_1$–$C_{18}$haloalkyl, $NO_2$, OH, CN, $OR_8$ or by halogen, and $R_{15}$ is $C_1$–$C_{18}$alkyl, unsubstituted phenyl or phenyl mono- or poly-substituted by $C_1$–$C_{18}$alkyl, $C_1$–$C_{18}$haloalkyl, $NO_2$, OH, CN, $OR_8$ or by halogen.

6. A process for the preparation of a compound of formula I according to claim 1 wherein, in a first step, a nitrogen base of formula II $$NR_2R_3R_4 \qquad (II)$$

is reacted with an a-haloalkene of formula III

 (III)

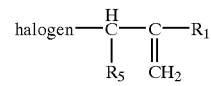

to form a compound of formula IV

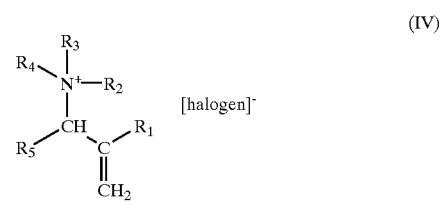 (IV)

and, in a second step, the compound of formula IV is reacted with a compound of formula V

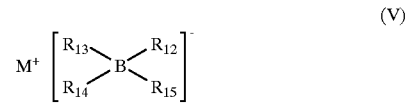 (V)

to form a compound of formula I wherein
halogen is bromine or iodine and
M is sodium, potassium or ammonium, and the radicals $R_1$, $R_2$, $R_3$, $R_4$, $R_5$, $R_{12}$, $R_{13}$, $R_{14}$ and $R_{15}$ are as defined in claim 1.

7. A composition comprising
A) at least one compound of formula (I) according to claim 1 and
B) at least one organic compound that is capable of a base-catalyzed addition or substitution reaction.

8. A composition according to claim 7, wherein component B) is an anionically polymerisable or crosslinkable organic material.

9. A composition according to claim 7, wherein component B) is one of the following systems:
a) an acrylate copolymer having alkoxysilane or alkoxysiloxane side groups;
b) a two-component system consisting of a hydroxy-group-containing polyacrylate and/or polyester and an aliphatic or aromatic polyisocyanate;
c) a two-component system consisting of a functional polyacrylate and a polyepoxide, the polyacrylate containing carboxy or anhydride groups;

d) a two-component system consisting of a fluorine-modified or silicone-modified hydroxy-group-containing polyacrylate or polyester and an aliphatic or aromatic polyisocyanate;

e) a two-component system consisting of a (poly)ketimine and an aliphatic or aromatic polyisocyanate;

f) a two-component system consisting of a (poly)ketimine and an unsaturated acrylate resin or an acetoacetate resin or methyl-α-acrylamido-methylglycolate;

h) a two-component system consisting of a (poly) oxazolidine and an anhydride-group-containing polyacrylate or an unsaturated acrylate resin or a polyisocyanate;

i) a two-component system consisting of an epoxy group-containing polyacrylate and a carboxy-group-containing polyacrylate;

l) a polymer based on an allyl-glycidyl ether;

m) a two-component system consisting of a (poly)alcohol and a (poly)isocyanate;

n) a two-component system consisting of an α,β-ethylenically unsaturated carbonyl compound and a compound having activated $CH_2$ groups.

10. A composition according to claim 7, wherein component B) is one of the following systems:

b) a two-component system consisting of a hydroxy-group-containing polyacrylate and/or polyester and an aliphatic or aromatic polyisocyanate;

c) a two-component system consisting of a functional polyacrylate and a polyepoxide, the polyacrylate containing carboxy or anhydride groups;

i) a two-component system consisting of an epoxy-group-containing polyacrylate and a carboxy-group-containing polyacrylate;

m) a two-component system consisting of a (poly)alcohol and a (poly)isocyanate;

n) a two-component system consisting of an α,β-ethylenically unsaturated carbonyl compound and a compound having activated $CH_2$ groups.

11. A composition according to claim 7, wherein component B is an epoxy resin or a mixture of different epoxy resins.

12. A composition according to claim 7, wherein component A) is present in an amount of from 0.01 to 10% by weight based on component B).

13. A composition according to claim 7 that in addition comprises a sensitiser selected from the thioxanthone, oxazine, acridine, phenazine and rhodamine group.

14. A method of carrying out a base-catalysed reaction, which comprises irradiating a composition according to claim 7 with light of a wavelength of from 200 nm to 650 nm.

15. A method according to claim 14, wherein heating is carried out during or after the irradiation.

16. A method according to claim 14 for the preparation of coatings, moulding materials or photostructured layers.

17. A coated substrate that is coated on at least one surface with a composition according to claim 7.

* * * * *